United States Patent
Kim et al.

(10) Patent No.: US 9,277,900 B2
(45) Date of Patent: Mar. 8, 2016

(54) X-RAY IMAGING APPARATUS

(71) Applicant: Samsung Electronics Co., Ltd., Suwon-si (KR)

(72) Inventors: Dae Soo Kim, Yongin-si (KR); Hyung Won Yoon, Seoul (KR); Jae Won Nam, Seongnam-si (KR); Young Jun Lee, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 81 days.

(21) Appl. No.: 14/143,172

(22) Filed: Dec. 30, 2013

(65) Prior Publication Data

US 2014/0192956 A1    Jul. 10, 2014

(30) Foreign Application Priority Data

Jan. 7, 2013  (KR) .......................... 10-2013-0001617
Jan. 7, 2013  (KR) .......................... 10-2013-0001830

(51) Int. Cl.
| | |
|---|---|
| *H05G 1/02* | (2006.01) |
| *H05G 1/04* | (2006.01) |
| *A61B 6/00* | (2006.01) |
| *A61B 6/04* | (2006.01) |
| *A61B 6/10* | (2006.01) |

(52) U.S. Cl.
CPC ............ *A61B 6/4464* (2013.01); *A61B 6/0464* (2013.01); *A61B 6/105* (2013.01); *A61B 6/4429* (2013.01); *A61B 6/4482* (2013.01)

(58) Field of Classification Search
CPC ............ A61B 6/00; A61B 6/105; A61B 6/44; A61B 6/4429; A61B 6/4452; A61B 6/4464; H05G 1/00; H05G 1/02; H05G 1/04; F16H 25/20; F16H 2025/204; B23Q 1/00; B23Q 1/25; B23Q 1/26; B23Q 1/262; B23Q 1/267; B23Q 1/28; B23Q 1/282; B23Q 1/285; B23Q 1/44; B23Q 1/56; B23Q 1/606; B23Q 1/62; B23Q 1/64; F16D 27/00; F16D 27/01; F16D 27/12; F16D 27/14; F16D 63/00; F16D 63/002; F16D 65/00; F16D 65/0006; F16D 65/0018; F16D 65/02; F16D 65/04; F16D 65/06; F16D 65/14; F16D 2121/00; F16D 2121/18; F16D 2121/20; F16D 2121/22
USPC ................ 378/193, 197, 204, 210; 74/89.32, 74/89.33; 248/637, 638, 646, 651, 656; 188/267, 271

See application file for complete search history.

(56) References Cited

U.S. PATENT DOCUMENTS

| | | | | |
|---|---|---|---|---|
| 2,673,626 A | * | 3/1954 | Bastin ........................... | 188/165 |
| 2,906,880 A | | 9/1959 | Stava et al. | |
| 2,950,394 A | * | 8/1960 | Stava et al. ...................... | 378/65 |
| 4,030,579 A | * | 6/1977 | Sell .............................. | 188/171 |

(Continued)

FOREIGN PATENT DOCUMENTS

| | | | | |
|---|---|---|---|---|
| EP | 1157661 | 11/2001 | | |
| GB | 715568 A | * 9/1954 | .............. | A61B 6/00 |
| GB | 2026206 | 1/1980 | | |

OTHER PUBLICATIONS

Extended European Search Report dated May 16, 2014 from European Patent Application No. 14150262.5, 11 pages.

*Primary Examiner* — Anastasia Midkiff
(74) *Attorney, Agent, or Firm* — Staas & Halsey LLP (57) ABSTRACT

An X-ray imaging apparatus having an improved structure to reduce noise generated when a position of an X-ray generator is fixed in position includes an X-ray generator, an X-ray detector, a moving carriage coupled with one end of the X-ray generator, a guide rail, and a holding unit disposed at an inner side of the moving carriage to hold the position of the X-ray generator, wherein the holding unit includes a contact pad to contact the guide rail to hold the moving carriage, a magnetic body to move the contact pad using magnetic force, and a holding plate coupled to the contact pad to move according to operation of the magnetic body and including a buffer material capable of absorbing noise or vibration.

22 Claims, 9 Drawing Sheets

(56) References Cited

U.S. PATENT DOCUMENTS

| | | |
|---|---|---|
| 2001/0053203 A1 | 12/2001 | Ishii et al. |
| 2008/0116351 A1* | 5/2008 | Dave et al. .................... 248/646 |
| 2012/0104283 A1* | 5/2012 | Dirauf et al. ................ 250/492.1 |
| 2013/0287533 A1* | 10/2013 | Manes ....................... 414/749.6 |

\* cited by examiner

X-RAY IMAGING APPARATUS

CROSS-REFERENCE TO RELATED APPLICATIONS

This application claims the priority benefit of Korean Patent Application No. 10-2013-0001830, filed on Jan. 7, 2013, and Korean Patent Application No. 10-2013-0001617, filed on Jan. 7, 2013, in the Korean Intellectual Property Office, the disclosures of which are incorporated herein by reference.

BACKGROUND

1. Field

The following description relates to an X-ray imaging apparatus having an improved structure to reduce noise generated when a position of an X-ray generator is fixed, or held, such that a movement of the X-ray generator is restricted.

2. Description of the Related Art

In general, medical X-ray imaging apparatuses are imaging systems to acquire an image of the inside of the human body using X-rays. An X-ray imaging apparatus irradiates an imaging site, such as head parts, chest parts, or the like of the human body, with X-rays and detects X-rays having passed through the imaging site, thereby acquiring an image of the inside of the human body.

The X-ray imaging apparatus includes an X-ray tube to irradiate an imaging site with X-rays, a high voltage generator to generate a high voltage needed for generation of X-rays, a moving device to change emission position and direction of X-rays, and the like. In addition, the X-ray imaging apparatus includes an operating device to enable an inspector to control these devices.

The X-ray imaging apparatus includes an X-ray detector to receive the emitted X-rays, convert the received X-rays into digital signals, and transmit the digital data to a PC. The X-ray detector may be installed at a stand for performing X-ray imaging at which a patient stands or on a patient table for performing X-ray imaging on which a patient lays. The X-ray detector may be used in a held state. Recently, however, a detachable X-ray detector may be manufactured and thus the detachable X-ray detector may be used in both the stand and the patient table.

In a conventional X-ray imaging apparatus, however, noise is generated due to contact between a guide rail and magnetic bodies when the X-ray generator or the X-ray detector performs a holding operation.

SUMMARY

Therefore, it is an aspect of the present disclosure to provide an X-ray imaging apparatus that may reduce noise generated when at least one of an X-ray generator and an X-ray detector performs a holding operation.

Additional aspects of the invention will be set forth in part in the description which follows and, in part, will be obvious from the description, or may be learned by practice of the invention.

In accordance with an aspect of the present disclosure, an X-ray imaging apparatus includes an X-ray generator to generate and emit X-rays, an X-ray detector to detect X-rays emitted from the X-ray generator, a moving carriage coupled with one end of the X-ray generator to adjust a position of the X-ray generator, a guide rail to move the moving carriage to change the position of the X-ray generator, and a holding unit disposed at an inner side of the moving carriage to hold the position of the X-ray generator, wherein the holding unit includes a contact pad to contact the guide rail to hold the moving carriage, a magnetic body to move the contact pad using magnetic force, and a holding plate coupled to the contact pad to move according to operation of the magnetic body and including a buffer material capable of absorbing noise or vibration.

The holding plate may include a plurality of layers, and at least one of the layers may be formed of a rubber material.

At least one of the layers of the holding plate may be formed of a magnetic material to enable the holding plate to move by movement of the magnetic body.

The at least one of the layers of the holding plate may be formed of steel.

The layers of the holding plate may include a layer contacting the magnetic body and a layer contacting the contact pad, the layers being formed of steel, and a layer of rubber disposed between the layers formed of steel.

The layers of the holding plate may include a layer contacting the magnetic body, the layer being formed of a magnetic material, and a layer contacting the contact pad, the layer being formed of a non-magnetic material.

The contact pad may be formed of urethane rubber.

The holding plate may further include a first elastic member disposed between the holding plate and the magnetic body to move by more than a predetermined interval according to operation of the magnetic body.

The X-ray imaging apparatus may further include a bracket to accommodate the magnetic body and guide coupling with the moving carriage.

The X-ray imaging apparatus may further include at least one shaft to guide coupling between the holding plate and the bracket.

The X-ray imaging apparatus may further include a second elastic member to prevent the bracket from being spaced apart by more than a predetermined distance and at least one third elastic member coupled to an end of the at least one shaft to reduce vibration or noise of the holding unit.

The guide rail may include a first guide rail and a second guide rail, the first and second guide rails being perpendicular to each other.

The holding unit may be coupled to contact at least one of the first guide rail and the second guide rail.

In accordance with an aspect of the present disclosure, an X-ray imaging apparatus includes an X-ray generator to generate and emit X-rays, an X-ray detector to detect X-rays emitted from the X-ray generator, a guide rail to change a position of the X-ray generator, a moving carriage having a first end movably coupled to the guide rail and a second end coupled to the X-ray generator, a magnetic body disposed at an inner side of the moving carriage, a contact pad having a first state to hold the moving carriage by contacting the guide rail according to operation of the magnetic body and a second state to move the moving carriage by being spaced apart from the guide rail, and a holding plate coupled to the contact pad and including a layer contacting the magnetic body and a layer contacting the contact pad, the layers being formed of a magnetic material, and a layer of a rubber material disposed therebetween to reduce vibration or noise so that the holding plate is spaced apart from the magnetic body in the first state and moves towards the magnetic body in the second state.

The X-ray imaging apparatus may further include a bracket to accommodate the magnetic body, a first elastic member disposed between the holding plate and the magnetic body to guide movement of the holding plate, and a second elastic member to prevent the magnetic body from being spaced apart from the guide rail by more than a predetermined distance.

The X-ray imaging apparatus may further include at least one shaft to couple the holding plate with the bracket and guide movement of the holding plate and at least one second elastic member coupled to an end of the shaft to reduce vibration and noise of the at least one shaft.

The magnetic material of the holding plate may be steel.

The contact pad may be formed of urethane rubber.

In accordance with an aspect of the present disclosure, an X-ray imaging apparatus includes an X-ray generator to generate and emit X-rays, an X-ray detector to detect X-rays emitted from the X-ray generator, a guide rail to move at least one of the X-ray generator and the X-ray detector, and a holding unit to hold a position of at least one of the X-ray generator and the X-ray detector and installed to contact the guide rail, wherein the holding unit includes a contact pad to hold the X-ray generator by contacting the guide rail, a magnetic body to move the contact pad using magnetic force, and a holding plate coupled to the contact pad to move according to operation of the magnetic body, wherein the holding plate includes three layers, the three layers including a first layer contacting the contact pad and a third layer contacting the magnetic body, the first and third layers being formed of a magnetic material, and a second layer disposed between the first and third layers, the second layer being formed of a viscoelastic material.

The contact pad may have a first state to hold at least one of the X-ray generator and the X-ray detector by contacting the guide rail and a second state to move at least one of the X-ray generator and the X-ray detector by the contact pad spaced apart from the guide rail, by operation of the magnetic body.

The contact pad may be formed of urethane rubber.

The first and third layers of the holding plate may be formed of steel, and the second layer of the holding plate may be formed of a rubber material.

The X-ray imaging apparatus may further include at least one shaft to couple the holding plate with a bracket accommodating the magnetic body, a first elastic member coupled to the at least one shaft to move the holding plate to the first state and the second state, a second elastic member coupled to an outer side of the bracket, and a third elastic member coupled to an end of another shaft to reduce vibration and noise due to movement of the holding plate.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Reference will now be made in detail to the embodiments of the present disclosure, examples of which are illustrated in the accompanying drawings, wherein like reference numerals refer to like elements throughout. An X-ray imaging apparatus according to an embodiment of the present disclosure may be applied to various kinds of X-ray imaging apparatuses. In the following description, a ceiling-type X-ray imaging apparatus in which a guide rail is installed on a ceiling of an inspection room will be described, as an example.

Figure 1:
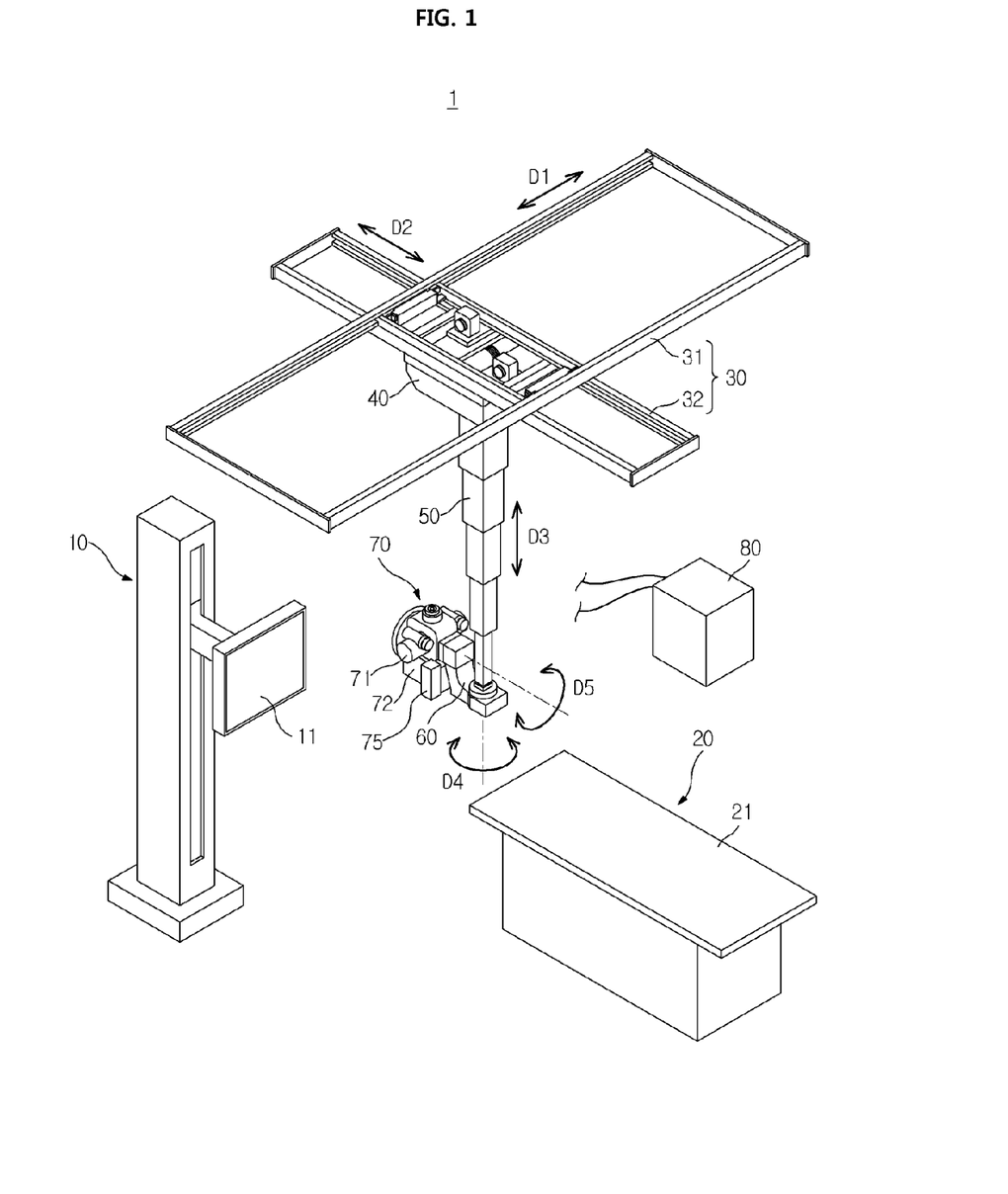
FIG. 1 is a diagram illustrating a main structure of an X-ray imaging apparatus according to an embodiment of the present disclosure.

FIG. 1 is a diagram illustrating a main structure of an X-ray imaging apparatus 1 according to an embodiment of the present disclosure.

As illustrated in FIG. 1, the X-ray imaging apparatus 1 includes a guide rail 30, a moving carriage 40, a post frame 50, an X-ray generator 70, and a driving device (not shown).

The guide rail 30 includes a first guide rail 31 and a second guide rail 32 that are installed to form a predetermined angle with respect to each other. The first guide rail 31 and the second guide rail 32 may extend in a direction perpendicular to each other.

The first guide rail 31 is installed on a ceiling of an inspection room in which the X-ray imaging apparatus 1 is placed. The second guide rail 32 is disposed below the first guide rail 31 and installed to slidably move along the first guide rail 31. The first guide rail 31 may be provided with a roller (not shown) that is movable along the first guide rail 31. The second guide rail 32 may be connected to the roller (not shown) to be movable along the first guide rail 31.

A direction in which the first guide rail 31 extends is defined as a first direction D1, and a direction in which the second guide rail 32 extends is defined as a second direction D2. Thus, the first and second directions D1 and D2 may be perpendicular to each other and parallel to the ceiling of the inspection room.

The moving carriage 40 is disposed below the second guide rail 32 to be movable along the second guide rail 32. The moving carriage 40 may be provided with a roller (not shown) arranged to move along the second guide rail 32.

The post frame 50 is disposed below and attached to the moving carriage 40. The post frame 50 may include a plurality of posts. The posts may be connected to one another so that the length of the posts increases or decreases in an upper or lower direction of the inspection room when the post frame 50 is attached to the moving carriage 40. A direction in which the length of the post frame 50 increases or decreases is defined as a third direction D3. Thus, the third direction D3 may be perpendicular to the first direction D1 and the second direction D2.

The X-ray generator 70 irradiates an object with X-rays. The X-ray generator 70 may be an X-ray tube included in a general X-ray imaging apparatus. The X-ray tube may include an X-ray generation source 71 to generate X-rays and a collimator 72 to guide the generated X-rays to the object (not shown).

Rotary joints 75 and 60 are disposed between the X-ray generator 70 and the post frame 50. The rotary joints 75 and 60 couple the X-ray generator 70 to the post frame 50 and support a load acting on the X-ray generator 70. The rotary joints 75 and 60 may include a first rotary joint 60 connected to a lower end of the post frame 50 and a second rotary joint 75 connected to the X-ray generator 70.

The first rotary joint 60 is rotatably installed about a central axis of the post frame 50 extending in an upper or lower direction of the inspection room. Thus, the first rotary joint 60 may rotate on a plane perpendicular to the third direction D3. In this regard, a direction in which the first rotary joint 60 rotates may be defined as a fourth direction D4, and the fourth direction D4 is a rotation direction of an axis parallel to the third direction D3.

The second rotary joint 75 is rotatably installed on a plane perpendicular to the ceiling of the inspection room. Thus, the second rotary joint 75 may rotate in a rotation direction of an axis parallel to the first direction D1 or the second direction D2. In this regard, a direction in which the second rotary joint 75 rotates may be defined as a fifth direction D5, and the fifth direction D5 is a rotation direction of an axis extending in the first or second direction D1 or D2.

The X-ray generator 70 may be connected to the first and second rotary joints 60 and 75 so that the X-ray generator 70 rotatably moves in the fourth and fifth directions D4 and D5. In addition, the X-ray generator 70 may be connected to the post frame 50 by the first and second rotary joints 60 and 75 so that the X-ray generator 70 linearly moves in the first, second, and third directions D1, D2, and D3.

To move the X-ray generator 70 in the first through fifth directions D1 through D5, driving devices (not shown) are installed. The driving devices may be electrically driven motors. The driving devices may be respectively connected to power transmission members (not shown) to linearly or rotatably move the X-ray generator 70 in the first through fifth directions D1 through D5. The power transmission member (not shown) may be a belt and a pulley, a chain and a sprocket, or a shaft, for example.

The X-ray imaging apparatus 1 may further include X-ray detectors 11 and 21 or an imaging stand 10 and a patient table 20 that may include the X-ray detectors 11 and 21, respectively. The X-ray detectors 11 and 21 may be designed for simultaneous use in the imaging stand 10 and the patient table 20. The patient table 20 may be movably installed.

The X-ray detectors 11 and 21 receive X-rays having been generated from the X-ray imaging apparatus 1 and passed through the object (not shown) and convert the received X-rays into electrical signals in accordance with the intensity of the X-rays, thereby performing real-time diagnosis.

In addition, the X-ray imaging apparatus 1 may further include a high voltage generator 80 to generate a high voltage needed for generation of X-rays.

Figure 2:
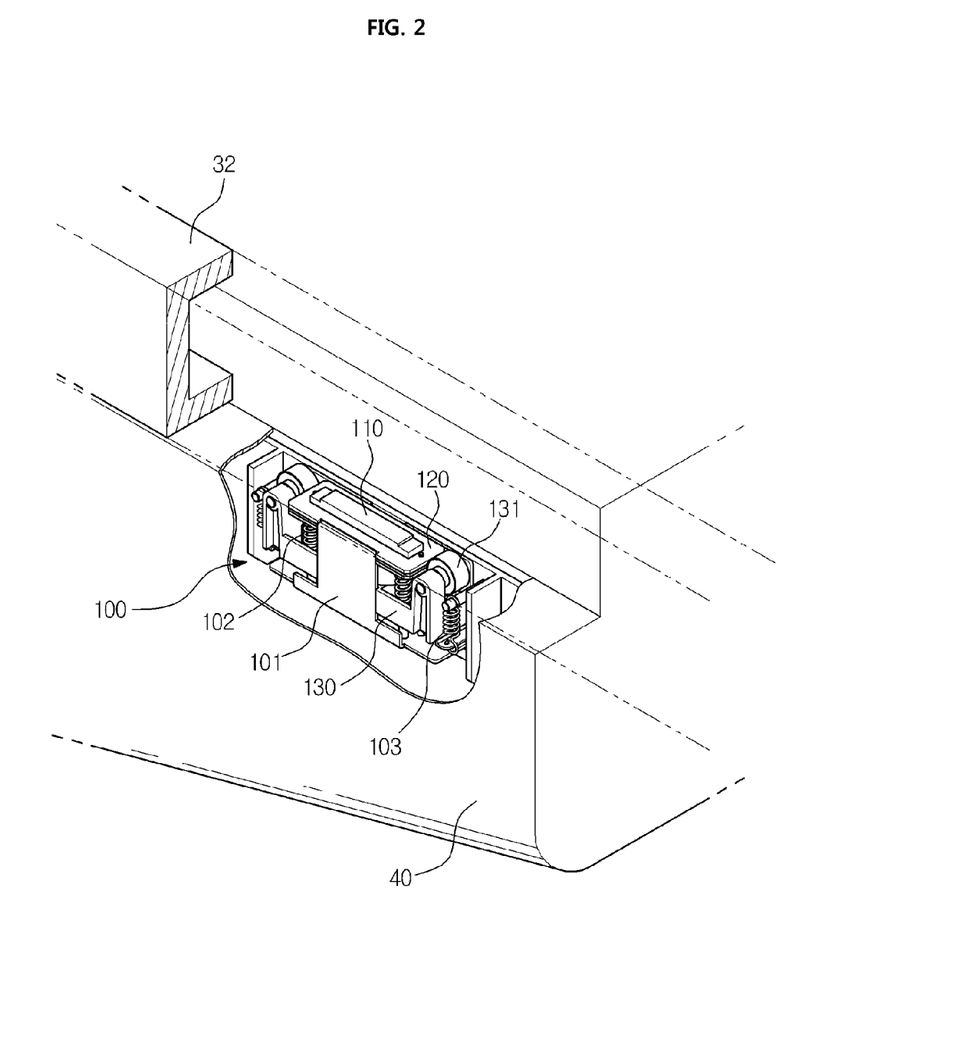
FIG. 2 is a diagram partially illustrating an inner side of a moving carriage, according to an embodiment of the present disclosure.
Figure 3:
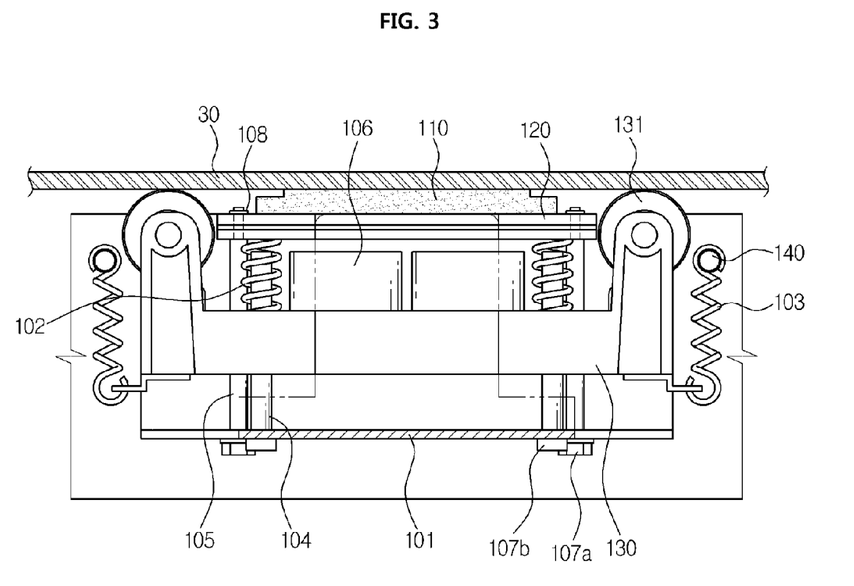
FIG. 3 is an enlarged view of a holding unit, according to an embodiment of the present disclosure.
Figure 4:
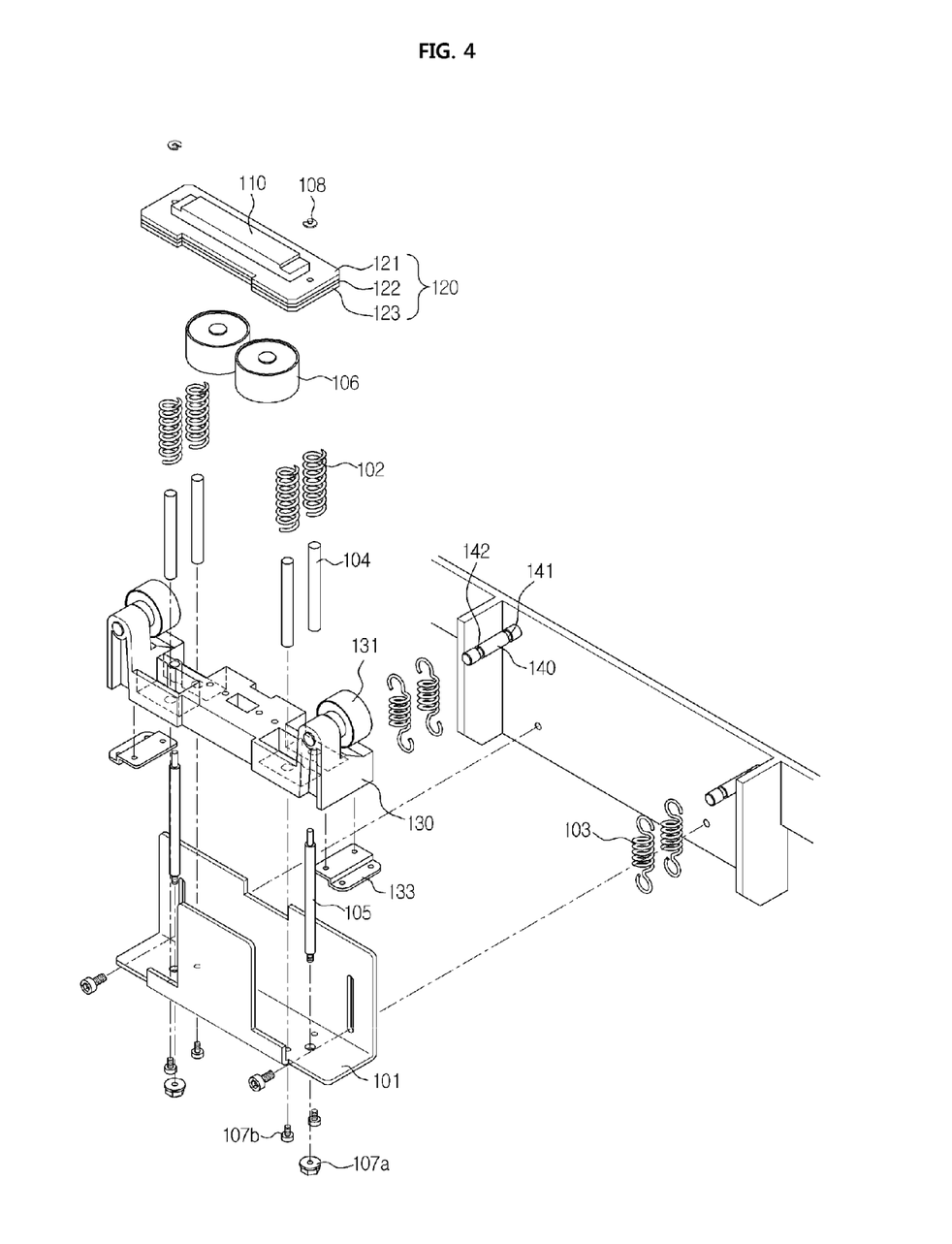
FIG. 4 is an exploded view of the holding unit, according to an embodiment of the present disclosure.

FIG. 2 is a diagram partially illustrating an inner side of the moving carriage 40, according to an embodiment of the present disclosure. FIG. 3 is an enlarged view of a holding unit 100, according to an embodiment of the present disclosure. FIG. 4 is an exploded view of the holding unit 100, according to an embodiment of the present disclosure.

As illustrated in FIGS. 2 through 4, the moving carriage 40 is provided at an inner side thereof with the holding unit 100. The holding unit 100 may contact at least one of the first and second guide rails 31 and 32. Referring to the drawings, the holding unit 100 is disposed below the second guide rail 32. Thus, the holding unit 100 contacts the second guide rail 32 and thus holds the moving carriage 40 coupled to the X-ray generator 70, so that the position of the X-ray generator 70 is fixed.

The holding unit 100 may be provided at an upper side thereof with at least one roller 131 to be coupled with the guide rail 30 and, accordingly, the X-ray generator 70 and the holding unit 100 move together. In addition, the holding unit 100 may be provided at the upper side thereof with a contact pad 110 to contact the guide rail 30 and thus hold the X-ray generator 70 by friction therebetween. In the ceiling type X-ray imaging apparatus according to an embodiment of the present disclosure, the guide rail 30 is disposed on the ceiling of the inspection room and therefore the contact pad 110 is disposed at the upper side of the holding unit 100, but embodiments of the present disclosure are not limited thereto. That is, the contact pad 110 may be disposed at any position that enables the contact pad 100 to contact the guide rail 30. The contact pad 110 may be made of a flexible material to relieve impact generated when contacting the guide rail 30. For example, as the flexible material, a urethane rubber material with flexibility and wear resistance may be used.

An operating state of the contact pad 110 may be changed to a first state to hold the X-ray generator 70 according to operation of a driving unit and a second state to release the X-ray generator 70. In the first state, the contact pad 110 contacts the guide rail 30 and thus holds the X-ray generator 70 by friction therebetween.

The holding unit 100 includes a driving unit to convert the operating state of the contact pad 110 to the first and second states. When the contact pad 110 is moved by magnetic force, the driving unit may include a magnetic body 106. According to the embodiments illustrated in the drawings, a holding plate 120 is driven by a pair of magnetic bodies 106. In a case in which the driving unit includes the magnetic bodies 106, the magnetic bodies 106 operate when current flows and do not operate when current does not flow.

The contact pad 110 may be coupled to the holding plate 120. Thus, the contact pad 110 moves according to movement of the holding plate 120. When the driving unit includes the magnetic bodies 106, at least a portion of the holding plate 120 may be made of a magnetic material because the holding plate 120 should be moved by magnetic force. In this case, the holding plate 120 may move according to operation of the magnetic bodies 106, and thus, it is unnecessary to form the guide rail 30 using a magnetic material as in the related art and the guide rail 30 may be made of a non-magnetic material. Accordingly, manufacturing costs may be reduced.

In addition, to reduce vibration and noise generated when the contact pad 110 contacts the guide rail 30, the holding plate 120 may be made of a buffer material. For example, the holding plate 120 may be formed of a viscoelastic material. This will be described below. In addition, the holding plate 120 may be formed of a plurality of materials and thus include a plurality of layers 121, 122, and 123. The layers 121, 122, and 123 may be coupled to one another by a fastening member 108.

The magnetic bodies 106 may be accommodated in a bracket 130. The bracket 130 may be provided with at least one roller 131 coupled thereto. The bracket 130 may be coupled to one side of the moving carriage 40. The moving carriage 40 may be provided at one side surface thereof with at least one coupling protrusion 140 to be coupled with the bracket 130. The coupling protrusion 140 may be provided at a surface thereof with a first groove 141 and a second groove 142 that are concave inwardly to enhance coupling strength between the holding unit 100 and the moving carriage 40.

The bracket 130 and the holding plate 120 may be coupled to each other by at least one shaft 104. A shaft to hold the holding plate 120 to the bracket 130 may be defined as a first shaft 104. An elastic member may be coupled to the first shaft 104. The elastic member coupled to the first shaft 104 may be defined as a first elastic member 102. When the driving unit does not operate, the contact pad 110 may be spaced apart from the holding plate by elastic restoring force of the first elastic member 102.

A support unit 101 may be disposed below the bracket 130 to prevent the driving unit from being spaced apart from the contact pad 110 by more than a predetermined interval. When the contact pad 110 and the magnetic bodies 106 are spaced apart from each other by more than a predetermined distance because the guide rail 30 is bent, magnetic force is weakened and thus, even though the magnetic bodies 106 operate normally, it may be difficult for the contact pad 110 to immediately move towards the guide rail 30 or in a direction opposite to the guide rail 30. To prevent this, the support unit 101 prevents the contact pad 110 and the magnetic bodies 106, which are driving units, from being spaced apart from each other by more than a predetermined distance. The holding plate 120, the bracket 130, and the support unit 101 are coupled by at least one shaft. The shaft that couples the holding plate 120 with the bracket 130 and the support unit 101 is defined as a second shaft 105.

The bracket 130 may be provided at outer sides thereof with second elastic members 103 to prevent the magnetic bodies 106 from being spaced apart from the guide rail 30 by more than a predetermined distance. Each second elastic member 103 may have a first end coupled to the moving carriage 40 and a second end coupled to a first end of the bracket 130.

The second elastic members 103 may be coupled to the first and second grooves 141 and 142 of the coupling protrusion 140 so that the holding unit 100 is stably coupled to the moving carriage 40 even when the holding unit 100 moves.

According to an embodiment of the present disclosure, the bracket 130 may be provided at opposite sides thereof with coupling members 133 and each coupling member 133 may be coupled with the second elastic members 103 so that the bracket 130 and the second elastic members 103 are indirectly coupled with each other. Thus, the second elastic members 103 may prevent the holding unit 100 from falling by more than a predetermined distance.

Fastening members may be coupled to lower ends of the first and second shafts 104 and 105. For example, as the fastening members, nuts 107*a* and bolts 107*b* may be used.

Figure 5:
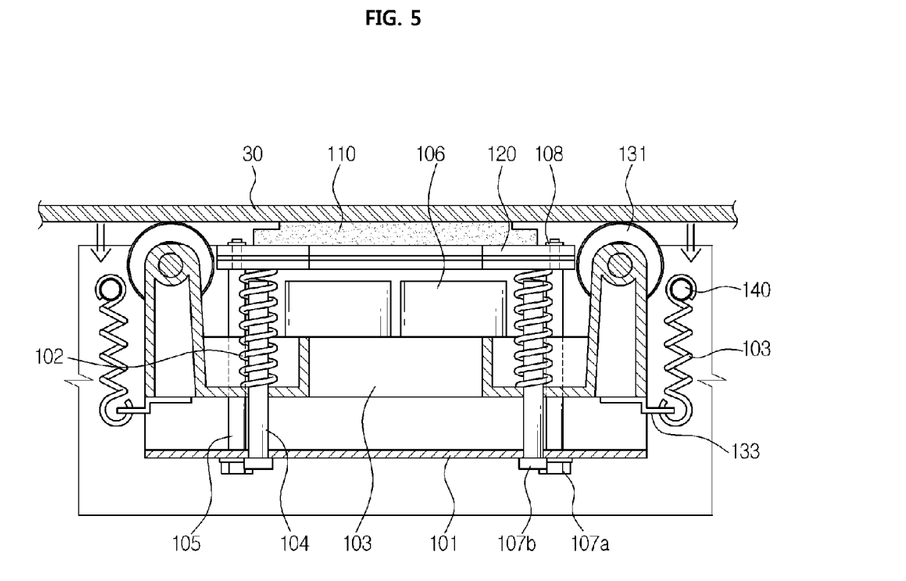
FIG. 5 is a diagram illustrating a state in which an X-ray generator is held in position by the holding unit, according to an embodiment of the present disclosure.
Figure 6:
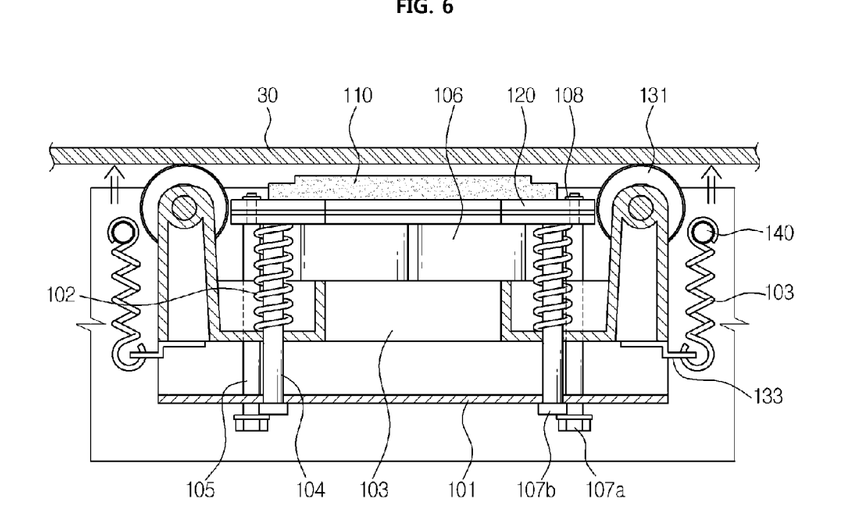
FIG. 6 is a diagram illustrating a state in which the X-ray generator is released by the holding unit, according to an embodiment of the present disclosure.

FIG. 5 is a diagram illustrating a state in which the X-ray generator 70 is held in a fixed position by the holding unit 100, according to an embodiment of the present disclosure. FIG. 6 is a diagram illustrating a state in which the X-ray generator 70 is released by the holding unit 100, according to an embodiment of the present disclosure.

Hereinafter, a process for holding and releasing the X-ray generator 70 using the holding unit 100, according to an embodiment of the present disclosure, will be described.

As illustrated in FIG. 5, when current does not flow in the magnetic bodies 106, the holding plate 120 is moved towards the guide rail 30 by elastic restoring force of the first elastic members 102. Accordingly, the contact pad 110 is also moved towards the guide rail 30 to contact the guide rail 30. Consequently, friction occurs between the contact pad 110 and the guide rail 30, thereby holding the X-ray generator 70 in position.

As illustrated in FIG. 6, when current flows in the magnetic bodies 106, the magnetic bodies 106 operate and magnetic force that is stronger than the elastic restoring force of the first elastic members 102 acts on the holding plate 120, and thus, the holding plate 120 is attracted by the magnetic force. Accordingly, the contact pad 110 coupled to the holding plate 120 also moves towards the magnetic bodies 106. Consequently, a space occurs between the contact pad 110 and the guide rail 30 and thus there is no friction therebetween and, as a result, the X-ray generator 70 may be moved.

Figure 7:
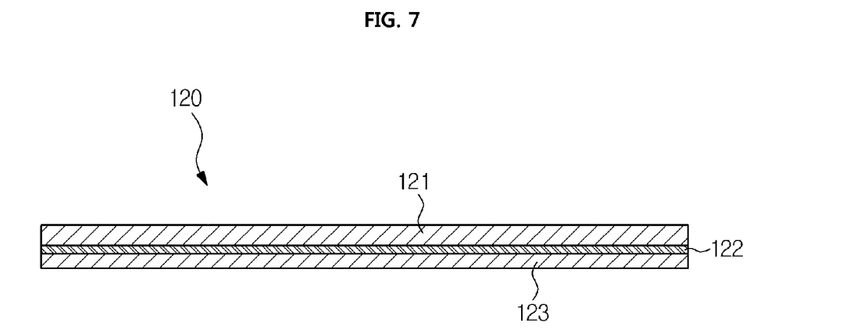
FIG. 7 is a view of a holding plate, according to an embodiment of the present disclosure.

FIG. 7 is a view of the holding plate 120, according to an embodiment of the present disclosure.

As illustrated in FIG. 7, the holding plate 120 may include three layers. The holding plate 120 may include a viscoelastic material to reduce noise generated when moving the holding unit 100.

Because the holding plate 120 should move according to operation of the magnetic bodies 106, at least one of the three layers of the holding plate 120 is formed of a magnetic material. The uppermost layer, the lowermost layer, and the middle layer of the holding plate 120 are defined as a first layer 121, a third layer 123, and a second layer 122, respectively. The first layer 121 contacts the contact pad 110, and the third layer 123 is a layer that is most affected by magnetic force caused by operation of the magnetic bodies 106.

The third layer 123 may be formed of a magnetic material to enable movement of the holding plate 120 by magnetic force of the magnetic bodies 106. For example, the third layer 123 may be formed of steel such as SS400. The first layer 121 may also be formed of the same material as that of the third layer 123. The second layer 122 is a layer formed for absorption of vibration and noise. To absorb vibration and noise, the second layer 122 may be formed of a rubber material.

As described above, the holding plate 120 includes the three layers and may have a sandwiched structure in which the layer for absorption of vibration and noise is disposed between the other two layers. The second layer 122 reduces noise more than that in the related art.

Figure 8:
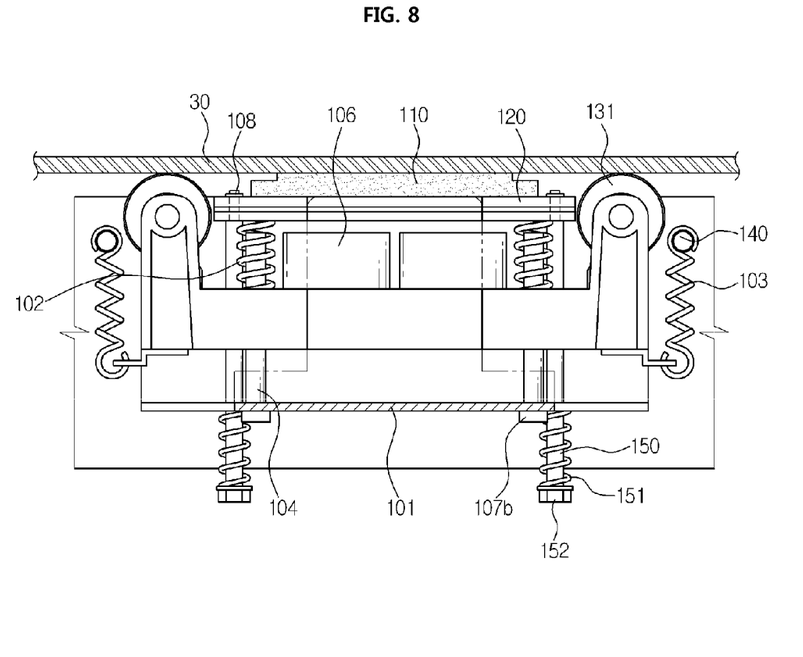
FIG. 8 is a view of a holding unit, according to an embodiment of the present disclosure.
Figure 9:
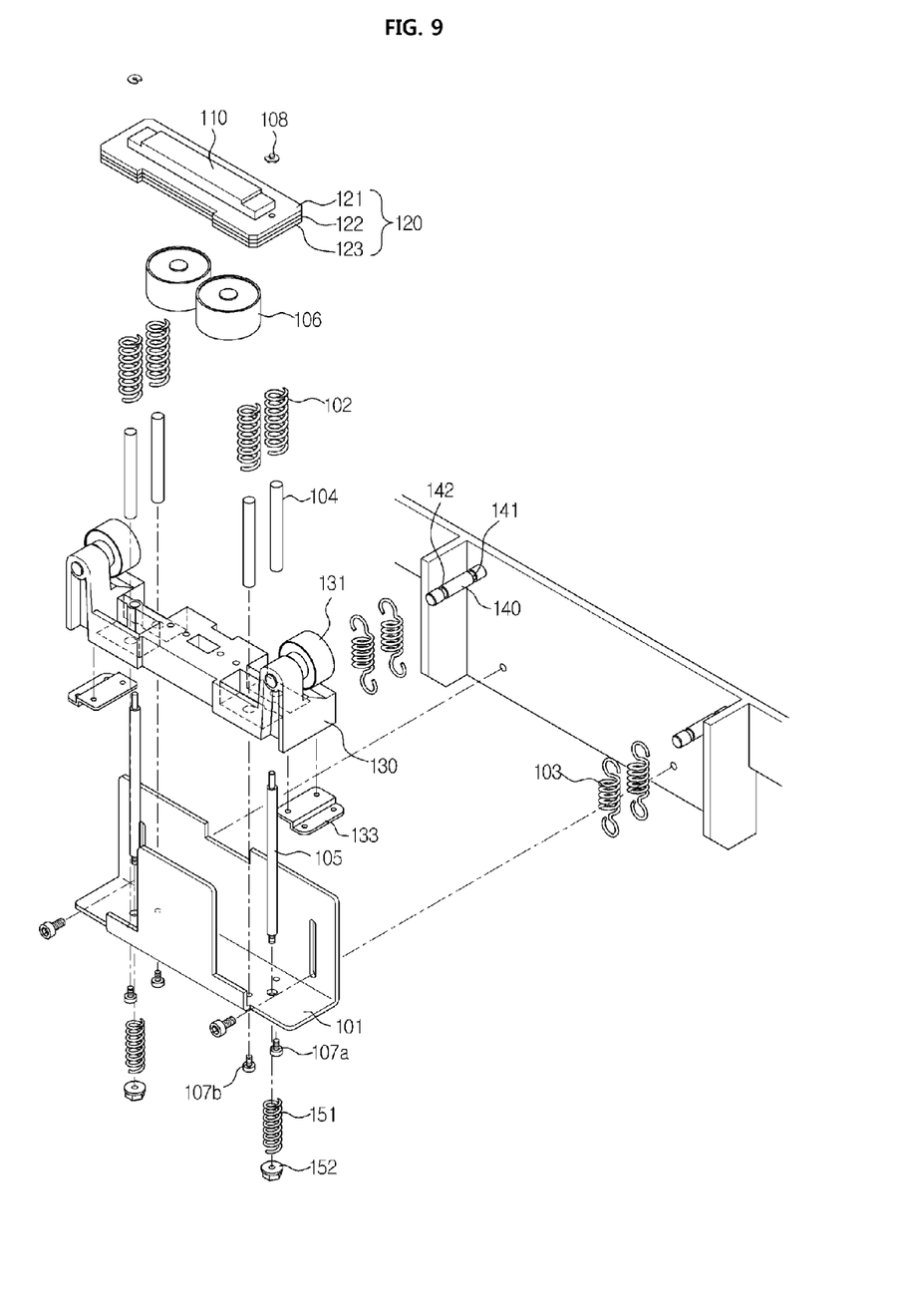
FIG. 9 is an exploded view of the holding unit according to the embodiment illustrated in FIG. 8.

FIG. 8 is a view of the holding unit 100, according to an embodiment of the present disclosure. FIG. 9 is an exploded view of the holding unit 100 according to the embodiment illustrated in FIG. 8.

In FIGS. 8 and 9, the same reference numerals as those of FIGS. 2 though 6 denote the same elements as those illustrated in FIGS. 2 through 6, and thus, a detailed description thereof is omitted.

Second shafts 105 may each have an end to which is coupled a third elastic member 151 for reducing vibration or noise generated in the holding unit 100. The third elastic members 151 may absorb vibration generated due to vibration of the second shafts 105 when the holding plate 120 is moved. The third elastic members 151 may be coupled to a lower side of the support unit 101. In addition, the second shafts 105 may be coupled with the respective third elastic members 151 using nuts 152.

Table 1 below shows experimental results of a degree of noise generated when the holding unit 100 according to an embodiment of the present disclosure having the above-described sandwiched structure and including the third elastic members 151 is used and when a general holding plate is used. The case when the general holding plate is used is denoted as Comparative Example, and the embodiment of the present disclosure is denoted as Example. In Example, the first and third layers 121 and 123 of the holding plate 120 are made of SS400, and the second layer 122 thereof is made of rubber.

TABLE 1

|  | Comparative Example | Example |
| --- | --- | --- |
| Noise generated when magnetic bodies operate (on state) | 76.1 dBA | 63.8 dBA |
| Noise generated when magnetic bodies do not operate (off state) | 84.1 dBA | 56.9 dBA |

As shown in Table 1, it can be confirmed that the noise generated in the on state in which the contact pad is spaced apart from the guide rail is decreased by 12.3 dBA from 76.1 dBA to 63.8 dBA as compared to the general case.

In addition, it can be confirmed that the noise generated in the off state in which the contact pad contacts the guide rail is decreased by 27.2 dBA from 84.1 dBA to 56.9 dBA.

As described above, according to the embodiment of the present disclosure, effects of reducing noise may be confirmed.

As is apparent from the above description, according to the one or more embodiments of the present disclosure, noise due to contact between a contact pad and a guide rail may be reduced, and noise and vibration due to contact between a holding plate and magnetic bodies may be reduced.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An X-ray imaging apparatus comprising:
    an X-ray generator to generate and emit X-rays;
    an X-ray detector to detect X-rays emitted from the X-ray generator;
    a moving carriage coupled with one end of the X-ray generator to adjust a position of the X-ray generator;
    a guide rail on which to move the moving carriage to change the position of the X-ray generator; and
    a holding unit disposed on the moving carriage to hold the position of the X-ray generator,
    wherein the holding unit comprises:
    a contact pad to contact the guide rail to hold the moving carriage;
    a magnetic body to move the contact pad using magnetic force; and
    a holding plate coupled to the contact pad to move according to operation of the magnetic body and comprising a noise-absorbing or vibration-reducing buffer material.

2. The X-ray imaging apparatus according to claim 1, wherein the holding plate comprises a plurality of layers, and at least one of the layers comprises a rubber material.

3. The X-ray imaging apparatus according to claim 2, wherein at least one of the layers of the holding plate comprises a magnetic material to enable the holding plate to move by movement of the magnetic body.

4. The X-ray imaging apparatus according to claim 3, wherein the at least one of the layers of the holding plate comprises steel.

5. The X-ray imaging apparatus according to claim 4, wherein the layers of the holding plate comprise a first steel layer contacting the magnetic body and a second steel layer contacting the contact pad, and a layer of rubber disposed between the first and second steel layers.

6. The X-ray imaging apparatus according to claim 3, wherein the layers of the holding plate comprise a magnetic layer contacting the magnetic body, and a non-magnetic layer contacting the contact pad.

7. The X-ray imaging apparatus according to claim 1, wherein the contact pad comprises urethane rubber.

8. The X-ray imaging apparatus according to claim 1, wherein the holding plate further comprises a first elastic member disposed between the holding plate and the magnetic body to move the holding plate by more than a predetermined interval according to operation of the magnetic body.

9. The X-ray imaging apparatus according to claim 1, further comprising a bracket to accommodate the magnetic body.

10. The X-ray imaging apparatus according to claim 9, further comprising at least one shaft.

11. The X-ray imaging apparatus according to claim 10, further comprising a first elastic member to prevent the bracket from being spaced apart from the guide rail by more than a predetermined distance and at least one second elastic member coupled to an end of the at least one shaft to reduce vibration or noise of the holding unit.

12. The X-ray imaging apparatus according to claim 1, wherein the guide rail comprises a first guide rail and a second guide rail, the first and second guide rails being perpendicular to each other.

13. An X-ray imaging apparatus comprising:
    an X-ray generator to generate and emit X-rays;
    an X-ray detector to detect X-rays emitted from the X-ray generator;
    a guide rail to change a position of the X-ray generator;
    a moving carriage having a first end movably coupled to the guide rail and a second end coupled to the X-ray generator;
    a magnetic body disposed on the moving carriage;
    a contact pad having a first state to hold the moving carriage by contacting the guide rail according to operation of the magnetic body and a second state to move the moving carriage by being spaced apart from the guide rail; and
    a holding plate coupled to the contact pad and comprising a first magnetic layer contacting the magnetic body and a second magnetic layer contacting the contact pad, and a layer of a rubber material disposed therebetween to reduce vibration or noise so that the holding plate is spaced apart from the magnetic body in the first state and moves towards the magnetic body in the second state.

14. The X-ray imaging apparatus according to claim 13, further comprising a bracket to accommodate the magnetic body, a first elastic member disposed between the holding plate and the magnetic body to guide movement of the holding plate, and a second elastic member to prevent the magnetic body from being spaced apart from the guide rail by more than a predetermined distance.

15. The X-ray imaging apparatus according to claim 14, further comprising at least one shaft to couple the holding plate with the bracket and guide movement of the holding plate and at least one third elastic member coupled to an end of the shaft to reduce vibration and noise of the at least one shaft.

16. The X-ray imaging apparatus according to claim 14, wherein the magnetic material of the holding plate comprises steel.

17. The X-ray imaging apparatus according to claim 13, wherein the contact pad comprises urethane rubber.

18. An X-ray imaging apparatus comprising:
an X-ray generator to generate and emit X-rays;
an X-ray detector to detect X-rays emitted from the X-ray generator;
a guide rail to move at least one of the X-ray generator and the X-ray detector; and
a holding unit to hold a position of at least one of the X-ray generator and the X-ray detector and installed to contact the guide rail,
wherein the holding unit comprises:
a contact pad to hold the X-ray generator by contacting the guide rail;
a magnetic body to move the contact pad using magnetic force; and
a holding plate coupled to the contact pad to move according to operation of the magnetic body,
wherein the holding plate comprises three layers, the three layers comprising a first layer contacting the contact pad and a third layer contacting the magnetic body, the first and third layers comprising a magnetic material, and a second layer disposed between the first and third layers, the second layer comprising a viscoelastic material.

19. The X-ray imaging apparatus according to claim 18, wherein the contact pad has a first state to hold at least one of the X-ray generator and the X-ray detector by contacting the guide rail and a second state to move at least one of the X-ray generator and the X-ray detector by the contact pad spaced apart from the guide rail, by operation of the magnetic body.

20. The X-ray imaging apparatus according to claim 18, wherein the contact pad comprises urethane rubber.

21. The X-ray imaging apparatus according to claim 18, wherein the first and third layers of the holding plate are comprised of steel, and the second layer of the holding plate comprises a rubber material.

22. The X-ray imaging apparatus according to claim 19, further comprising at least one shaft to couple the holding plate with a bracket accommodating the magnetic body, a first elastic member coupled to the at least one shaft to move the holding plate to the first state from the second state, a second elastic member coupled to an outer side of the bracket, and a third elastic member coupled to an end of another shaft to reduce vibration and noise due to movement of the holding plate.

* * * * *